US012397129B2

(12) United States Patent
Welch et al.

(10) Patent No.: US 12,397,129 B2
(45) Date of Patent: Aug. 26, 2025

(54) CORONARY GUIDE CATHETER

(71) Applicant: NorMedix, Inc., Eden Prairie, MN (US)

(72) Inventors: Jeffrey M. Welch, Maple Grove, MN (US); Gregg Stuart Sutton, Maple Grove, MN (US)

(73) Assignee: NorMedix, Inc., Eden Prairie, MN (US)

( * ) Notice: Subject to any disclaimer, the term of this patent is extended or adjusted under 35 U.S.C. 154(b) by 187 days.

(21) Appl. No.: 17/668,725

(22) Filed: Feb. 10, 2022

(65) Prior Publication Data

US 2022/0233810 A1 Jul. 28, 2022

Related U.S. Application Data

(63) Continuation of application No. 15/224,323, filed on Jul. 29, 2016, now abandoned.

(Continued)

(51) Int. Cl.
A61M 25/00 (2006.01)
A61M 25/06 (2006.01)

(52) U.S. Cl.
CPC ...... A61M 25/005 (2013.01); A61M 25/0045 (2013.01); A61M 25/0041 (2013.01); A61M 25/0662 (2013.01)

(58) Field of Classification Search
CPC ............ A61M 25/005; A61M 25/0041; A61M 25/0045; A61M 25/0662; A61M 2025/0681; A61M 2025/0047
See application file for complete search history.

(56) References Cited

U.S. PATENT DOCUMENTS 4,493,329 A 1/1985 Crawford et al.
4,737,153 A * 4/1988 Shimamura ....... A61M 16/0425
138/131

(Continued)

FOREIGN PATENT DOCUMENTS

CA 2994262 C 9/2023
EP 0810003 A2 12/1997

(Continued)

OTHER PUBLICATIONS

"U.S. Appl. No. 15/224,323, Appeal Brief filed Feb. 15, 2021", 22 pgs.

(Continued)

Primary Examiner — Bradley J Osinski
(74) Attorney, Agent, or Firm — Schwegman Lundberg & Woessner, P.A.

(57) ABSTRACT

Embodiments include an interventional guide catheter, comprising: a main tubular shaft with a distal tip and proximal end; the main tubular shaft comprising: a main inner structural layer comprising a metallic helically wound multi-filar wire extending from a proximal tube termination to a distal end, a braided wire layer covering the main inner structural layer that extends from the proximal tube termination to the distal end, an outer layer of polymer jacketing fixedly attached to the main inner structural layer and braid layer, an inner layer of polymer jacketing and fixedly attached to the main inner structural layer, a distal tip made of layers of polymer, a distal end curve shape for anatomical conformance that is heat processed in the main metal portion of the structure; and a lamination of the inner layer, main inner structural layer, braided wire layer and outer layer. Other embodiments are also included herein.

12 Claims, 5 Drawing Sheets

Related U.S. Application Data

(60) Provisional application No. 62/199,050, filed on Jul. 30, 2015.

(56) References Cited

U.S. PATENT DOCUMENTS

| | | |
|---|---|---|
| 5,106,363 A | 4/1992 | Nobuyoshi |
| 5,472,435 A | 12/1995 | Sutton |
| 5,558,652 A | 9/1996 | Henke |
| 5,573,522 A | 11/1996 | Houser et al. |
| 5,658,264 A | 8/1997 | Samson |
| 5,695,483 A | 12/1997 | Samson |
| 5,755,704 A | 5/1998 | Lunn |
| 5,795,341 A | 8/1998 | Samson |
| 5,846,229 A * | 12/1998 | Berg ............... A61M 25/0041 604/528 |
| 5,853,400 A | 12/1998 | Samson |
| 5,876,386 A | 3/1999 | Samson |
| 5,891,112 A | 4/1999 | Samson |
| 5,891,114 A | 4/1999 | Chien et al. |
| 5,947,940 A * | 9/1999 | Beisel ............... A61M 25/005 604/526 |
| 5,951,929 A | 9/1999 | Wilson et al. |
| 5,957,910 A | 9/1999 | Holden, II et al. |
| 6,042,578 A | 3/2000 | Dinh et al. |
| 6,053,903 A | 4/2000 | Samson |
| 6,053,904 A | 4/2000 | Scribner et al. |
| 6,103,037 A | 8/2000 | Wilson |
| 6,143,013 A | 11/2000 | Samson et al. |
| 6,152,911 A | 11/2000 | Giannoble |
| 6,165,163 A | 12/2000 | Chien et al. |
| 6,217,565 B1 | 4/2001 | Cohen |
| 6,355,027 B1 | 3/2002 | Le et al. |
| 6,368,316 B1 | 4/2002 | Jansen et al. |
| 6,374,476 B1 | 4/2002 | Ponzi et al. |
| 6,451,005 B1 | 9/2002 | Saitou |
| 6,464,684 B1 | 10/2002 | Galdonik |
| 6,562,022 B2 | 5/2003 | Hoste et al. |
| 6,589,227 B2 | 7/2003 | Sonderskov |
| 6,616,651 B1 | 9/2003 | Stevens |
| 6,626,889 B1 | 9/2003 | Simpson et al. |
| 6,629,952 B1 | 10/2003 | Chien et al. |
| 6,635,047 B2 | 10/2003 | Forsberg |
| 6,689,120 B1 * | 2/2004 | Gerdts ............... A61M 25/005 604/526 |
| 6,702,972 B1 | 3/2004 | Markle |
| 6,709,429 B1 | 3/2004 | Schaefer et al. |
| 6,740,073 B1 | 5/2004 | Saville |
| 6,824,553 B1 | 11/2004 | Samson et al. |
| 6,866,660 B2 | 3/2005 | Garabedian et al. |
| 6,942,654 B1 | 9/2005 | Schaefer et al. |
| 7,018,372 B2 | 3/2006 | Casey et al. |
| 7,025,758 B2 | 4/2006 | Klint |
| 7,104,979 B2 | 9/2006 | Jansen et al. |
| 7,117,703 B2 | 10/2006 | Kato et al. |
| 7,331,948 B2 | 2/2008 | Skarda |
| 7,354,428 B1 | 4/2008 | Gosiengfiao et al. |
| 7,455,739 B2 | 11/2008 | Zhou |
| 7,507,229 B2 | 3/2009 | Hewitt et al. |
| 7,534,317 B2 | 5/2009 | Brustad et al. |
| 7,597,830 B2 | 10/2009 | Zhou |
| 7,615,043 B2 | 11/2009 | Zhou |
| 7,637,902 B2 | 12/2009 | Eversull et al. |
| 7,674,239 B2 | 3/2010 | Sisken et al. |
| 7,704,245 B2 | 4/2010 | Dittman et al. |
| 7,713,259 B2 | 5/2010 | Gosiengfiao et al. |
| 7,744,587 B2 | 6/2010 | Murphy |
| 7,763,012 B2 | 7/2010 | Petrick et al. |
| 7,815,762 B2 | 10/2010 | Lentz et al. |
| 7,824,392 B2 | 11/2010 | Zhou |
| 7,833,218 B2 | 11/2010 | Lunn et al. |
| 7,850,623 B2 | 12/2010 | Griffin et al. |
| 7,909,779 B2 | 3/2011 | Shimogami et al. |
| 7,909,812 B2 | 3/2011 | Jansen |
| 7,914,515 B2 | 3/2011 | Heideman et al. |
| 7,955,313 B2 | 6/2011 | Boismier |
| 7,968,038 B2 | 6/2011 | Dittman et al. |
| 8,021,352 B2 | 9/2011 | Slazas et al. |
| 8,034,045 B1 | 10/2011 | Lyons |
| 8,070,898 B2 | 12/2011 | Eversull et al. |
| 8,100,881 B2 | 1/2012 | Hoffa |
| 8,114,144 B2 | 2/2012 | Chow et al. |
| 8,142,415 B2 | 3/2012 | Warnock, Jr. et al. |
| 8,157,790 B2 | 4/2012 | Kubo |
| 8,182,466 B2 | 5/2012 | Stehr et al. |
| 8,206,373 B2 | 6/2012 | Zhou |
| 8,251,976 B2 | 8/2012 | Zhou |
| 8,257,314 B2 | 9/2012 | Agnew |
| 8,317,772 B2 | 11/2012 | Jansen et al. |
| 8,343,136 B2 | 1/2013 | Howat et al. |
| 8,348,925 B2 | 1/2013 | Fischell et al. |
| 8,366,699 B2 | 2/2013 | Jimenez |
| 8,377,035 B2 | 2/2013 | Zhou et al. |
| 8,431,057 B2 | 4/2013 | Guo et al. |
| 8,475,431 B2 | 7/2013 | Howat |
| 8,486,048 B2 | 7/2013 | Kubo et al. |
| 8,529,719 B2 | 9/2013 | Pingleton et al. |
| 8,535,293 B2 | 9/2013 | Faherty et al. |
| 8,535,294 B2 | 9/2013 | Fischell et al. |
| 8,540,695 B2 | 9/2013 | Shimogami et al. |
| 8,591,495 B2 | 11/2013 | Fischell et al. |
| 8,636,270 B2 | 1/2014 | Ostrovsky |
| 8,647,323 B2 * | 2/2014 | Guo ............... A61M 25/0043 604/527 |
| 8,696,699 B2 | 4/2014 | Chomas et al. |
| 8,702,679 B2 | 4/2014 | Deckman et al. |
| 8,702,680 B2 | 4/2014 | Jimenez et al. |
| 8,708,997 B2 | 4/2014 | Parker |
| 8,721,625 B2 | 5/2014 | Klint |
| 8,758,326 B2 | 6/2014 | Hennissy |
| 8,858,530 B2 | 10/2014 | Nishigishi et al. |
| 8,864,744 B2 | 10/2014 | Howat et al. |
| 8,926,560 B2 | 1/2015 | Dinh et al. |
| 8,986,284 B2 | 3/2015 | Kuwada et al. |
| 9,114,229 B2 | 8/2015 | Fuentes |
| 9,254,374 B2 | 2/2016 | Thorstenson et al. |
| 9,259,550 B2 | 2/2016 | Schaeffer |
| 9,259,813 B2 | 2/2016 | Heideman |
| 9,278,191 B2 | 3/2016 | Nihonmatsu et al. |
| 2002/0068899 A1 | 6/2002 | James, Jr. et al. |
| 2002/0095102 A1 | 7/2002 | Winters |
| 2003/0009184 A1 | 1/2003 | Pepin |
| 2003/0191451 A1 | 10/2003 | Gilmartin |
| 2004/0092844 A1 | 5/2004 | Johnson et al. |
| 2005/0043713 A1 | 2/2005 | Zhou |
| 2005/0090802 A1 | 4/2005 | Connors, III et al. |
| 2006/0095050 A1 * | 5/2006 | Hartley ............ A61M 25/0662 606/108 |
| 2006/0111649 A1 | 5/2006 | Zhou |
| 2007/0233040 A1 | 10/2007 | Macnamara et al. |
| 2010/0217235 A1 | 8/2010 | Thorstenson et al. |
| 2012/0109078 A1 | 5/2012 | Schaeffer |
| 2012/0130217 A1 | 5/2012 | Kauphusman et al. |
| 2012/0172798 A1 | 7/2012 | Miller et al. |
| 2012/0277729 A1 | 11/2012 | Melsheimer |
| 2013/0018318 A1 | 1/2013 | Ravichandran et al. |
| 2013/0197481 A1 | 8/2013 | Guo et al. |
| 2013/0255062 A1 | 10/2013 | Howat |
| 2013/0289697 A1 | 10/2013 | Baker et al. |
| 2014/0046138 A1 | 2/2014 | Merk et al. |
| 2014/0214006 A1 | 7/2014 | Hiroshige et al. |
| 2014/0236124 A1 | 8/2014 | Miyata |
| 2014/0330253 A1 | 11/2014 | Weiss |
| 2014/0352871 A1 | 12/2014 | Wang et al. |
| 2015/0051541 A1 | 2/2015 | Kanemasa et al. |
| 2015/0119859 A1 | 4/2015 | Cajamarca et al. |
| 2015/0174363 A1 | 6/2015 | Sutermeister et al. |
| 2015/0217083 A1 | 8/2015 | Richter et al. |
| 2015/0231360 A1 | 8/2015 | Watanabe et al. |
| 2015/0258306 A1 | 9/2015 | Plassman et al. |
| 2015/0335857 A1 | 11/2015 | Ishikawa |
| 2016/0001040 A1 | 1/2016 | Yamaguchi et al. |

(56) References Cited

U.S. PATENT DOCUMENTS

2016/0121075 A1    5/2016   Schaeffer
2017/0028167 A1    2/2017   Welch et al.

FOREIGN PATENT DOCUMENTS

| | | |
|---|---|---|
| EP | 2687254 A1 | 1/2014 |
| EP | 3328476 B1 | 12/2019 |
| JP | H09506541 A | 6/1997 |
| JP | 2005537877 A | 12/2005 |
| JP | 2018522704 A | 8/2018 |
| WO | WO-0166176 A1 | 9/2001 |
| WO | WO-2006031874 A1 | 3/2006 |
| WO | WO-2014210427 A1 | 12/2014 |
| WO | WO-2017020012 A1 | 2/2017 |

OTHER PUBLICATIONS

"U.S. Appl. No. 15/224,323, Appeal Decision mailed Dec. 10, 2021", 9 pgs.
"U.S. Appl. No. 15/224,323, Examiners Answer mailed Mar. 19, 2021", 7 pgs.
"U.S. Appl. No. 15/224,323, Final Office Action mailed Jun. 7, 2019", 13 pgs.
"U.S. Appl. No. 15/224,323, Final Office Action mailed Jul. 14, 2020", 14 pgs.
"U.S. Appl. No. 15/224,323, Non Final Office Action mailed Jan. 8, 2020", 14 pgs.
"U.S. Appl. No. 15/224,323, Non Final Office Action mailed Mar. 26, 2018", 14 pgs.
"U.S. Appl. No. 15/224,323, Non Final Office Action mailed Nov. 23, 2018", 13 pgs.
"U.S. Appl. No. 15/224,323, Reply Brief mailed May 19, 2022", 9 pgs.
"U.S. Appl. No. 15/224,323, Response filed Jun. 8, 2020 to Non Final Office Action mailed Jan. 8, 2020", 14 pgs.
"U.S. Appl. No. 15/224,323, Response filed Dec. 9, 2019 to Final Office Action mailed Jun. 7, 2019", 15 pgs.
"U.S. Appl. No. 15/224,323, Response to Non Final Office Action mailed Mar. 26, 2018 filed Sep. 26, 2018", 13 pgs.
"U.S. Appl. No. 15/224,323, Response to Non Final Office Action mailed Nov. 23, 2018 filed Mar. 25, 2019", 11 pgs.
"Canadian Application Serial No. 2,994,262, Examiner's Rule 86(2) Requisition mailed Aug. 24, 2022", 6 pgs.
"Canadian Application Serial No. 2,994,262, Response filed Dec. 23, 2022 to Examiner's Rule 86(2) Requisition mailed Aug. 24, 2022", 38 pgs.
"European Application Serial No. 16748030.0, Communication Pursuant to Article 94(3) EPC mailed Nov. 28, 2018", 7 pgs.
"European Application Serial No. 16748030.0, Response filed Apr. 5, 2019 to Communication Pursuant to Article 94(3) EPC mailed Nov. 28, 2018", 35 pgs.
"European Application Serial No. 16748030.0, Response filed Oct. 1, 2018 to Communication Pursuant to Rules 161(1) and 162 EPC mailed Mar. 20, 2018", 22 pgs.
"International Application Serial No. PCT/US2016/044881, International Preliminary Report on Patentability mailed Feb. 8, 2018", 9 pgs.
"International Application Serial No. PCT/US2016/044881, International Search Report mailed Nov. 18, 2016", 6 pgs.
"International Application Serial No. PCT/US2016/044881, Written Opinion mailed Nov. 18, 2016", 7 pgs.
"Japanese Application Serial No. 2018-525532, Notification of Reasons for Refusal mailed Jul. 7, 2020", with English translation, 17 pages.
"Japanese Application Serial No. 2018-525532, Office Action mailed Feb. 9, 2021", with English translation, 14 pages.
"Japanese Application Serial No. 2018-525532, Response filed Jan. 6, 2021 to Notification of Reasons for Refusal mailed Jul. 7, 2020", with English claims, 7 pages.
"Japanese Application Serial No. 2018-525532, Response filed Aug. 6, 2021 to Office Action mailed Feb. 9, 2021", w/ English claims, 7 pgs.

\* cited by examiner

CORONARY GUIDE CATHETER

CLAIM OF PRIORITY

This application is a continuation of U.S. patent application Ser. No. 15/224,323, filed Jul. 29, 2016, which application claims the benefit of priority to U.S. Provisional Patent Application Ser. No. 62/199,050, filed Jul. 30, 2015, the contents of which are hereby incorporated by reference in their entireties.

FIELD OF THE TECHNOLOGY

The present application relates to coronary guide catheters. More specifically, the present application relates to guide catheters that are used to introduce therapeutic catheters, such as stent delivery systems.

BACKGROUND

Interventional guide catheters are used by physicians to place catheters, electrode leads and other therapeutic interventional devices to desired locations in the patient's body. The guide catheter provides support for device advancement (stents, balloons, etc.) for instance, to the coronary arteries. It is the main conduit for therapeutic device and guide wire transport and provides a means for injecting contract media. Guide catheters typically have a pre-shaped distal end that is configured to allow access and direction into the arterial branches. In coronary guide catheters, the distal end shapes also provide back-up support for device placement by using shapes made to "back-up" against aortic anatomy.

Guide catheters are made so that the distal shapes as much as possible, retain their shape during the procedure and don't soften in body temperature to any significant or detrimental degree. Guide catheters with distal end shapes also are typically made to provide end-to-end torque to allow "steering" the distal end into the artery. In addition, guide catheter are typically made to be relatively stiff so that there is no stretching and biasing during device passage. To achieve these performance criteria, current guide catheter construction means are usually polymer based with metallic wire braid reinforcement.

The problems associated with current interventional guide catheters include softening at body temperature thereby losing critical performance features like back-up support or torsion. In addition, guide catheters have been prone to kinking, buckling, ovaling and stretching, especially in long procedures or difficult, more tortuous anatomy.

SUMMARY

Embodiments disclosed herein include an interventional guide catheter for introducing interventional catheters into the vasculature, comprising: a main tubular shaft with a distal tip and proximal end; the main tubular shaft comprising: a main inner structural layer comprising a metallic helically wound multi-filar wire (wall thickness (0.0015-0.010") extending from a proximal tube termination to the distal end, a braided wire layer (0.0005-0.010" thick) covering the metallic helically wound multi-filar layer that extends from the proximal tube termination to the distal end, an outer layer of polymer jacketing covering and fixedly attached to the main metal structure and braid layer with wall thickness of 0.001-0.005", an inner layer of polymer jacketing covering and fixedly attached to the inner metal structure with wall thickness of 0.001-0.0005", a distal tip made of layers of polymer, the distal tip being 0.05-0.20" in length, an optional distal end curve shape for anatomical conformance that is heat processed in the main metal portion (e.g., one or more of the multi-filar layer, braid or the like) of the structure; and a lamination of the inner layer, metallic helically wound multi-filar layer, braid and outer layer that optionally does not comprise fusion of the outer and inner layers. The main metal portion is separately heat processed (e.g., to provide the distal end curve shape) prior to lamination in one example. In another example, the main metal portion is heat processed while incorporated with the other components of the catheter (e.g., the inner and outer layers, or the like).

In an embodiment, the main helically wound multi-filar layer terminates distally before the primary curve of the distal end. In another embodiment, the main helically wound layer terminates proximal to the distal end curve shape including the primary curve.

In an embodiment, the outer and inner layers are fused together through the main coil structure and braid.

In an embodiment, the metal helically wound multi-filar layer comprises stainless steel.

In an embodiment, the braid layer comprises stainless steel wire.

In an embodiment, the multi-filar structure comprises at least 6 filars and not more than 20 filars.

In an embodiment, the multi-filar structure wire has been swaged.

In an embodiment, the outer diameter of the main tubular shaft is at least 0.060 inches and not more than 0.115 inches.

In an embodiment, the outer layer comprises Pebax.

In an embodiment, the outer layer comprises nylon.

In an embodiment, the outer layer is coated with a hydrophilic polymer.

In an embodiment, the inner layer comprises PTFE.

In an embodiment, the inner layer comprises nylon.

In an embodiment, the inner layer is coated with a hydrophilic polymer.

In an embodiment, the distal tip comprises a PTFE inner layer and a Pebax outer layer.

In an embodiment, the metallic helically wound layer comprises welded terminations.

In an embodiment, the metallic helically wound layer comprises a distal end that comprises a gold coating.

In an embodiment, the gold coating is at least 0.5 mm and not more than 2 mm in length.

In an embodiment, the outer layer comprises at least two layers of Pebax.

In an embodiment, the outer layer is heat shrinkable to allow it to be formed tightly onto the metallic helically wound layer.

In an embodiment, the metallic helically wound wire has a rectangular cross-section.

In an embodiment, the metallic helically wound wire has a circular cross-section.

In an embodiment, the metallic helically wound layer wire has an oval or elliptical cross-section.

In an embodiment, the metallic helically wound layer wire has been coated with PTFE coating prior to forming into the multi-filar configuration.

In an embodiment, the main tubular shaft length is at least 60 cm and not more than 200 cm long.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present application is defined by the appended claims and their legal equivalents.

BRIEF DESCRIPTION OF THE FIGURES

The technology may be more completely understood in connection with the following drawings, in which.

Figure 1:
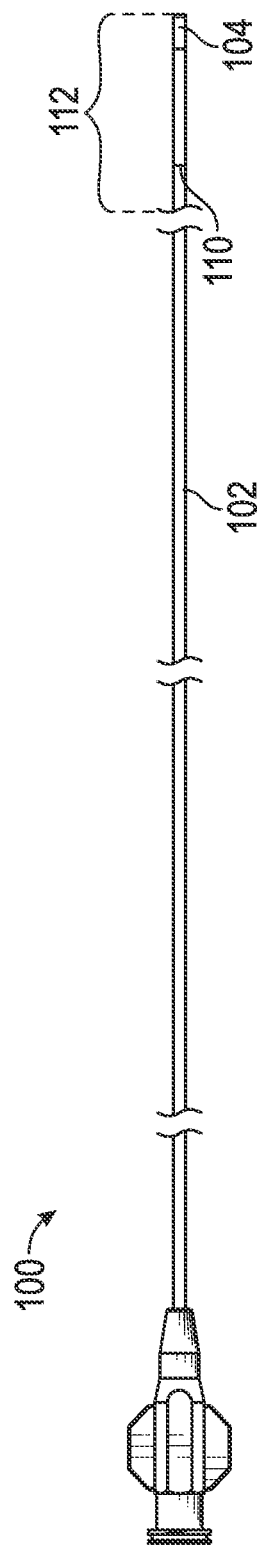
FIG. 1 is a front view of a guide catheter, according to an embodiment.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The guide catheter as described herein can solve the problems associated with current guide catheter technology by providing a novel design, construction and materials.

The guide catheter, described herein, can be used in interventional cases where significant arterial tortuosity is encountered such as using a radial artery access or using a femoral approach on an obese patient.

In various embodiments, the guide catheter can include a composite built tube that can be fabricated using a specially wound metal inner layer and jacketed with very thin layers of polymer inside and out. The metallic inner layer can be made using a multi-filar (6-20 filars) helically wound wire structure. In some embodiments, the helical structure can be swaged, such that each individual wire strand is partially rectangular in cross-section and therefore can result in a very tight/close fitting wire matrix. The helical structure can also be made using a non-swaged, round, square or rectangular wire.

In various embodiments, the wall thickness of the inner metal structure can range from 1.5 to 10 thousandths of an inch thick.

The helically wound metal structure can improve the mechanical integrity of the catheter tube, such as compared to current guide catheters with respect to kinking, buckling, flexibility, radial strength, and maintaining circularity of the catheter lumen cross-section.

This marked improvement can be achieved by the significant increase in the amount of metal in the catheter. For instance, current guide catheters that are composite built or wire braid reinforced have total cross-sectional metallic component in the range of 5-10%. The guide catheter as described herein can have a total cross-sectional metallic component of 40-60%. The transmission of mechanical energy through this significantly higher modulus composite can result in significantly higher performance.

The guide catheter of this invention also comprises an outer polymer layer and an inner polymer layer. In an embodiment, the outer polymer layer and the inner polymer layer can include one or more polymers, such as PTFE, Pebax, or Polyurethane. The polymer layers can be attached to the metal structure by thermal polymer heat-shrinking or reflow. The resultant wall thickness of the polymer layers can range from 0.5 to 3.0 thousandths of an inch for each layer.

In various embodiments, the guide catheter can include a pre-shaped curve, such as a curved distal end region. The guide catheter can attain the pre-shaped curve configuration by heat-setting the metal in this portion of the catheter. The result can include a curve that retains its shape in body temperature and over time does not substantially soften, such as soften enough to unintentionally change shape.

The guide catheter can further include a soft (low durometer) polymer distal tip, various distal curve shapes, a radiopaque distal marker band, and a proximal luer adapter. The guide catheter range in sizes from 4F to 8F and in lengths from 80 to 125 cm.

Figure 2:
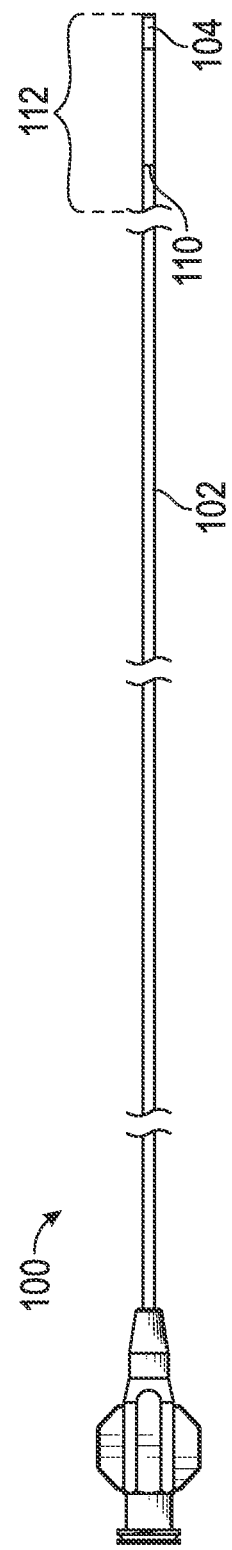
FIG. 2 is a back view of a guide catheter, according to an embodiment.
Figure 3:
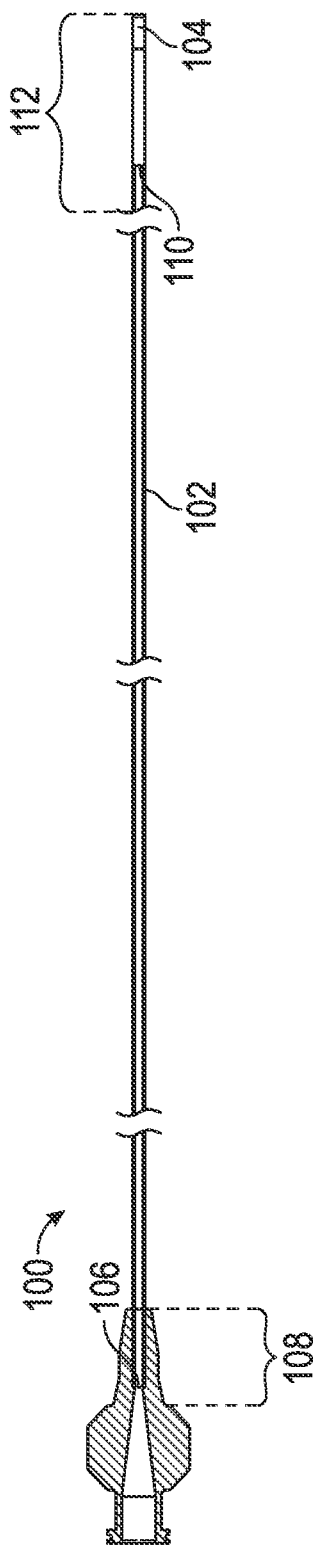
FIG. 3 is a cross-section view of a guide catheter, according to an embodiment.

In reference now to the figures, FIG. 1 shows a front view of a guide catheter 100, according to an embodiment. FIG. 2 shows a back view of the guide catheter 100. FIG. 3 shows a cross-sectional view of the guide catheter 100. In an embodiment, the guide catheter 100 can be configured for introducing interventional catheters into the vasculature of a patient.

In an embodiment, the catheter 100 can include a main tubular shaft 102 with a distal tip 104 and proximal end 106. The distal tip 104 can be on the opposite end of the tubular shaft 102 from the proximal end 106. The distal tip 104 can include at least one layer of polymer. In an embodiment, the distal tip 104 includes at least two layers of polymer. In an embodiment, the distal tip 104 can include an inner layer and an outer layer. In an embodiment, the inner layer of the distal tip 104 can include PTFE. In an embodiment, the outer layer of the distal tip 104 can include Pebax.

In an embodiment, the distal tip 104 can be at least 0.05 inches long. In an embodiment, the distal tip 104 can be at least 0.02 inches long. In an embodiment, the distal tip 104 can be 0.2 inches long or shorter. In an embodiment, the distal tip 104 can be 0.5 inches long or shorter. In various embodiments, the tubular shaft 102 can include a main inner structural layer.

The main inner structural layer can include a metallic helically wound multi-filar wire extending from a proximal tube termination (e.g., the proximal shaft end 106 or proximal shaft portion 108) to a distal end 112 including at least the bracketed 112 shown in FIGS. 1-3 (e.g., at the distal location). The main inner structural layer can further include a braided wire layer. In various embodiments, the braided wire layer can cover at least a portion of the outer portion (opposite from the inner lumen) of the metallic helically wound multi-filar layer that extends from the proximal tube termination to the distal end. In other embodiments, the braided wire layer is within the metallic helically wound multi-filar layer.

In various embodiments, the main tubular shaft 102 can include an outer layer. The outer layer can include a polymer. The outer layer can jacket, coat, or cover the outer surface of the main inner structural layer. The outer layer can be fixedly attached to the main inner structural layer.

In various embodiments, the main tubular shaft 102 can include an inner layer. The inner layer can include a polymer. The inner layer can jacket, coat, or cover the inner surface of the main inner structural layer. The inner layer can be fixedly attached to the main inner structural layer.

Figure 10:
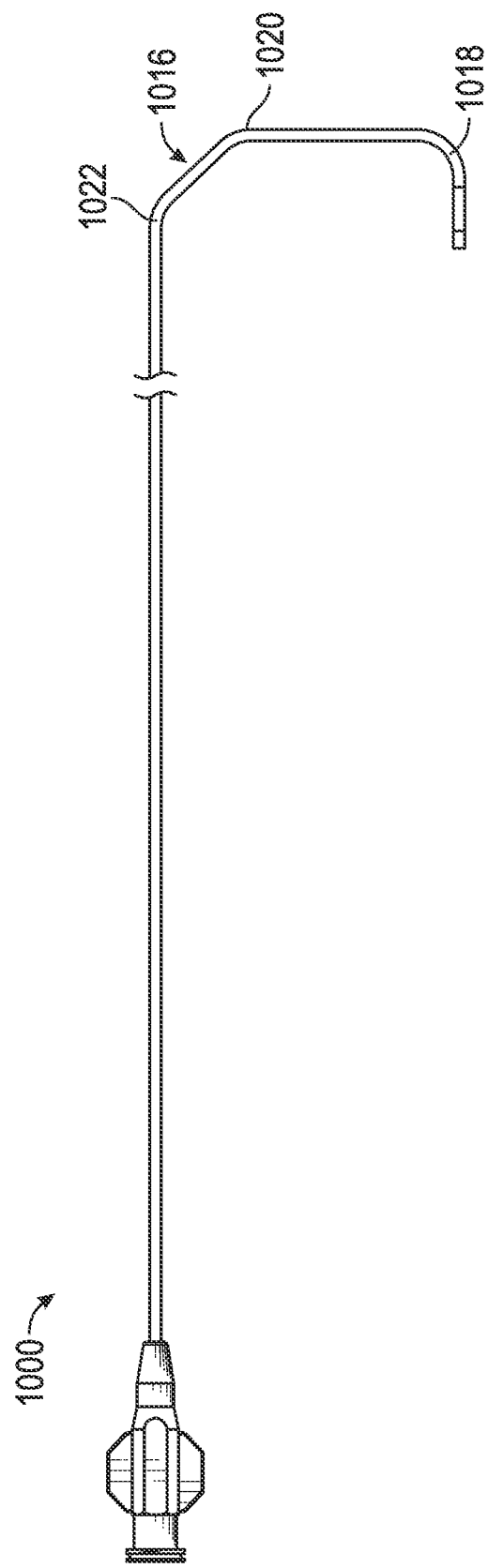
FIG. 10 is a front view of a guide catheter, according to an embodiment.

The main tubular shaft 102 can include a curve, such as on the distal end (shown in FIG. 10). The curve shape can be configured for anatomical conformance. The shape can be heat processed in the main tubular shaft 102, such as in the main inner structural layer or another metal portion. In an embodiment, the helically wound multi-filar layer terminates distally prior to the curve of the distal end. In another embodiment the helically wound multi-filar layer terminates proximal a primary curve of the curve (e.g., of the distal end curve shape) and distal to other portions of the curve including, but not limited to secondary and tertiary curves.

In various embodiments, the metallic helically wound multi-filar layer, and the braid can be laminated by the inner layer and the outer layer, such that the lamination does not fuse the outer layer and the inner layer together.

In an embodiment, the main tubular shaft 102 can be at least 60 cm long and not longer than 200 cm. In an embodiment, the main tubular shaft 102 can be at least 10 cm long and not longer than 300 cm. In an embodiment, the main tubular shaft 102 can be at least 30 cm long and not longer than 250 cm. In an embodiment, the main tubular shaft 102 can be at least 50 cm long and not longer than 225 cm.

In an embodiment, the main tubular shaft 102 can have an outer diameter of at least 0.060 inches and not more than 0.115 inches. In an embodiment, the main tubular shaft 102 can have an outer diameter of at least 0.060 inches. In an embodiment, the main tubular shaft 102 can have an outer diameter of at least 0.040 inches. In an embodiment, the main tubular shaft 102 can have an outer diameter of at least 0.050 inches. In an embodiment, the main tubular shaft 102 can have an outer diameter of at least 0.070 inches. In an embodiment, the main tubular shaft 102 can have an outer diameter of at least 0.080 inches.

In an embodiment, the main tubular shaft 102 can have an outer diameter of no greater than 0.115 inches. In an embodiment, the main tubular shaft 102 can have an outer diameter of no greater than 0.095 inches. In an embodiment, the main tubular shaft 102 can have an outer diameter of no greater than 0.105 inches. In an embodiment, the main tubular shaft 102 can have an outer diameter of no greater than 0.125 inches. In an embodiment, the main tubular shaft 102 can have an outer diameter of no greater than 0.135 inches.

Figure 4:
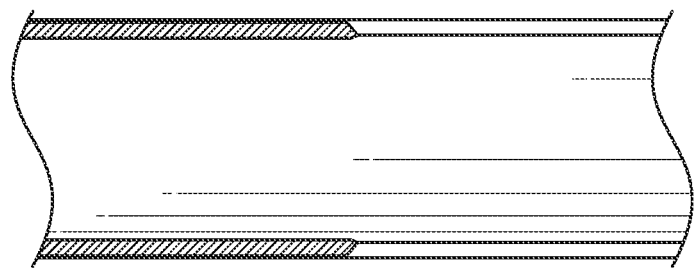
FIG. 4 is a cross-section view of a portion of a guide catheter, according to an embodiment.
Figure 5:
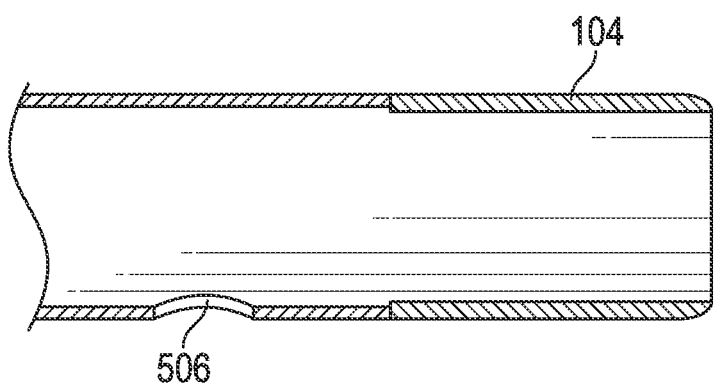
FIG. 5 is a cross-section view of a portion of a guide catheter, according to an embodiment.

FIG. 4 and FIG. 5 show cross-section views of portions of a guide catheter 100, according to various embodiments. FIG. 5 shows a cross-section of a portion of the distal tip 104. As seen in FIG. 5, the guide catheter 100 can define one or more apertures 506. In various embodiments, the main tubular shaft 102 can define an aperture 506. In an embodiment, the distal tip 104 can define an aperture 506.

Figure 7:
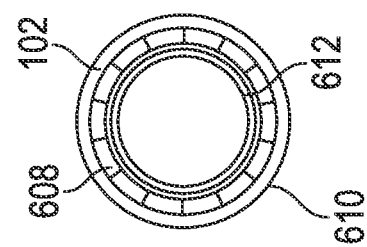
FIG. 7 is a cross-section view of a portion of a guide catheter, according to an embodiment.
Figure 6:
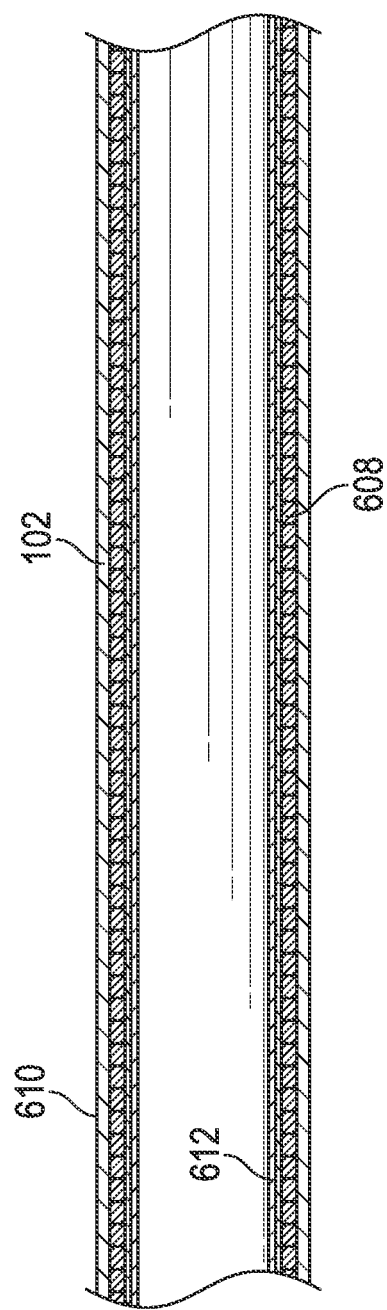
FIG. 6 is a cross-section view of a portion of a guide catheter, according to an embodiment.

FIG. 6 shows a cross-section view of a portion of the main tubular shaft 102, according to an embodiment. FIG. 7 shows a cross-section view from the end of the main tubular shaft 102. In an embodiment, the main tubular shaft 102, can include a main inner structural layer 608. The main inner structural layer 608 can include a metallic helically wound multi-filar wire. In various embodiments, the metallic helically wound multi-filar wire can include stainless steel. In various embodiments, the metallic helically wound multi-filar wire can be swaged.

In various embodiments, the metallic helically wound multi-filar wire can include at least 6 filars and not more than 20 filars. In various embodiments, the metallic helically wound multi-filar wire can include at least 4 filars and not more than 24 filars. In various embodiments, the metallic helically wound multi-filar wire can include at least 8 filars and not more than 18 filars. In various embodiments, the metallic helically wound wire can have a rectangular cross-section, a circular cross-section, an oval cross-section or an elliptical cross-section. In various embodiments, the metallic helically wound wire can have been substantially coated with PTFE coating prior to forming into the multi-filar configuration.

In an embodiment, the main inner structural layer 608 can include welded terminations. In an embodiment, the main inner structural layer 608 can include a distal end that includes a gold coating. In various embodiments, the gold coating can range from 0.5 mm thick to 2 mm in length. In various embodiments, the gold coating can range from 0.4 mm thick to 2.5 mm in length. In various embodiments, the gold coating can range from 0.25 mm thick to 3 mm in length.

In an embodiment, the main inner structural layer 608 can have a thickness that can range from 0.0015 inches to 0.010 inches (e.g., one or more of a consistent thickness or variable thicknesses). In an embodiment, the main inner structural layer 608 can have a thickness of at least 0.0010 inches. In an embodiment, the main inner structural layer 608 can have a thickness of at least 0.0005 inches. In an embodiment, the main inner structural layer 608 can have a thickness of no greater than 0.015 inches. In an embodiment, the main inner structural layer 608 can have a thickness of no greater than 0.020 inches. Optionally, the main inner structural layer 608 includes a varying wall thickness. For instance, the metallic helically wound multi-filar wire is ground so that portions of the layer have varying thickness. The catheter, in some examples includes corresponding reduced diameter based on the grinding of the metallic helically wound multi-filar wire. In still another example, the metallic helically wound multi-filar wire is formed with a varied diameter (e.g., is necked) to accordingly decrease the thickness of the main inner structural layer 608. In one example, a proximal portion of the main inner structural layer 608 includes a greater thickness relative to a distal portion to enhance pushability of the catheter. In another example, the distal portion of the main inner structural layer 608 has a lesser thickness than the proximal portion to facilitate bending and corresponding navigation through tortuous vasculature. In an embodiment, the main tubular shaft 102 can include an outer layer 610. The outer layer 610 can include a polymer. The outer layer 610 can jacket or cover at least a portion of the outer portion of the main inner structural layer 608. In an embodiment, the outer layer 610 can be at least 0.001 inches thick and not more than 0.005 inches thick. In an embodiment, the outer layer 610 can be at least 0.0007 inches thick. In an embodiment, the outer layer 610 can be at least 0.0005 inches thick. In an embodiment, the outer layer 610 can be no more than 0.007 inches thick. In an embodiment, the outer layer can be no more than 0.01 inches thick.

In an embodiment, the outer layer 610 can include Pebax. In an embodiment, the outer layer 610 can include nylon. In an embodiment, the outer layer 610 can be coated with a hydrophilic polymer. In an embodiment, the outer layer 610 can include at least two layers. In an embodiment, each of the two layers included in the outer layer 610 can include Pebax. In various embodiments, the outer layer 610 can be heat shrinkable, such as to allow the outer layer 610 to be formed tightly onto the main inner structural layer 608.

In an embodiment, the main tubular shaft 102 can include an inner layer 612. The inner layer 612 can include a polymer. The inner layer 612 can jacket or cover at least a portion of the inner portion of the main inner structural layer 608. In an embodiment, the inner layer 612 can be at least 0.001 inches thick and not more than 0.005 inches thick. In an embodiment, the inner layer 612 can be at least 0.0007 inches thick. In an embodiment, the inner layer 612 can be at least 0.0005 inches thick. In an embodiment, the inner layer 612 can be no more than 0.007 inches thick. In an embodiment, the inner layer can be no more than 0.01 inches thick.

In an embodiment, the inner layer 612 can include PTFE. In an embodiment, the inner layer 612 can include nylon. In an embodiment, the inner layer 612 can be coated with a hydrophilic polymer.

Figure 8:
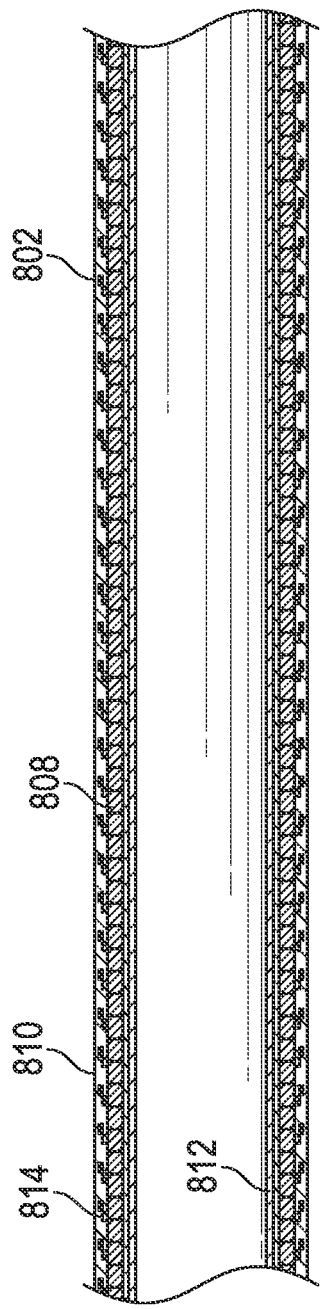
FIG. 8 is a cross-section view of a portion of a guide catheter, according to an embodiment.

In an embodiment, the outer layer 610 and the inner layer 612 can be fused together, such as through the main inner structural layer 608 and/or the braid 814 (shown in FIG. 8).

Figure 9:
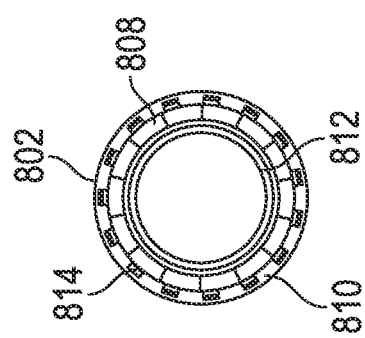
FIG. 9 is a cross-section view of a portion of a guide catheter, according to an embodiment.

FIG. 8 shows a cross-section view of a portion of the main tubular shaft 802, according to an embodiment. FIG. 9 shows a cross-section view from the end of the main tubular shaft 802.

In various embodiments, the main tubular shaft 802 can include a braided wire layer 814. In an embodiment, the braided wire layer 814 can be disposed between the main inner structural layer 808 and the outer layer 810. In an embodiment, the braided wire layer 814 can be disposed within a portion of the outer layer 810. In another embodiment, the braided wire layer 814 is provided within the main inner structural layer 808 (e.g., along the interior of the layer 808). Optionally, the braided wire layer 814 is between the inner layer 812 and the main inner structural layer 808.

The braided wire layer 814 can cover at least a portion of the main inner structural layer 808, such as the helically wound multi-filar layer. In an embodiment, the braided wire can include stainless steel.

In an embodiment, the braided wire layer 814 can be at least 0.0005 inches thick and not more than 0.010 inches thick. In an embodiment, the braided wire layer 814 can be at least 0.005 inches thick and not more than 0.010 inches thick. In an embodiment, the braided wire layer 814 can be at least 0.0004 inches thick. In an embodiment, the braided wire layer 814 can be at least 0.0003 inches thick. In an embodiment, the braided wire layer 814 can be no more than 0.015 inches thick. In an embodiment, the braided wire layer 814 can be no more than 0.020 inches thick.

FIG. 10 shows a front view of a guide catheter 1000, according to an embodiment. In an embodiment, the guide catheter 1000 can include a distal end curve 1016. The distal end curve 1016 can be configured for anatomical conformance. The distal end curve 1016 can be heat processed in the metal portion of the catheter 1000. In an embodiment, the main helically wound layer can terminate distally before a primary curve (e.g., one or more of curves 1018, 1020, 1022 or the like) of the distal end 112.

In various embodiments, the guide catheter can include a pre-shaped curve, such as a curved distal end region. The guide catheter can attain the pre-shaped curve configuration by heat-setting the metal in this portion of the catheter. The result can include a curve that retains its shape in body temperature and over time does not substantially soften, such as soften enough to unintentionally change shape.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference.

The technology has been described with reference to various specific and preferred embodiments and techniques. However, it should be understood that many variations and modifications may be made while remaining within the spirit and scope of the technology.

What is claimed is:

1. An interventional guide catheter for introducing interventional catheters into vasculature, comprising:
    a main tubular shaft extending between a proximal end and a distal end having a distal tip, the main tubular shaft including a catheter lumen configured for introducing catheters through the distal tip;
    wherein the main tubular shaft includes a sidewall having:
    an outer layer;
    an inner layer extending around the catheter lumen;
    a metal main inner structural layer including metal interposed between the outer and inner layer; and
    a braided wire layer surrounding the metal main inner structural layer, the braided wire layer within the outer layer; and
    wherein the outer layer, inner layer, metal main inner structural layer and the braided wire layer are a laminate, and the outer layer and inner layer are isolated from each other by layers consisting of one or more of the metal main inner structural layer or the braided wire layer.

2. The interventional guide catheter of claim 1, wherein the outer layer and inner layer isolated from each other includes the outer layer and inner layer are not fused.

3. The interventional guide catheter of claim 2, wherein the main inner structural layer includes a helically wound multi-filar wire.

4. The interventional guide catheter of claim 3, wherein the sidewall has a sidewall thickness including:
- an outer layer component thickness of around 0.001 to 0.005 inches;
- an inner layer component thickness of around 0.0005 to 0.0007 inches; and
- a main inner structural layer component thickness of around 0.0015 to 0.010 inches.

5. The interventional guide catheter of claim 4, wherein the braided wire layer has a braided wire layer thickness of around 0.0005 to 0.010 inches.

6. The interventional guide catheter of claim 5, wherein the braided wire layer thickness is around 0.005 to 0.010 inches.

7. The interventional guide catheter of claim 5, wherein the helically wound multi-filar wire includes distal and proximal edges, and the proximal edges of windings of the helically wound multi-filar wire are engaged with distal edges of proximate windings of the helically wound multi-filar wire.

8. The interventional guide catheter of claim 7, wherein the distal end includes a curve, and the main inner structural layer is absent from the curve of the distal end.

9. The interventional guide catheter of claim 7, wherein the distal end includes a curve, and the main inner structural layer is present in the curve of the distal end.

10. The interventional guide catheter of claim 7, wherein the helically wound multi-filar wire includes a swaged, round, square or rectangular cross-section.

11. The interventional guide catheter of claim 10, wherein a cross section of the main tubular shaft includes a cross-sectional metallic component of around 40 to 60 percent.

12. The interventional guide catheter of claim 11, wherein the braided wire layer includes a cross-sectional metallic component of around 5 to 10 percent of the cross section of the main tubular shaft.

* * * * *